United States Patent [19]

Hiller

[11] 4,235,878

[45] Nov. 25, 1980

[54] ANIMAL FEEDS CONTAINING A MIXTURE OF AVOPARCIN OR SPIRAMYCIN AND PROTEOLYTIC ENZYMES

[75] Inventor: Günter Hiller, Erkrath, Fed. Rep. of Germany

[73] Assignee: Henkel Kommanditgesellschaft auf Aktien (Henkel KGaA), Düsseldorf-Holthausen, Fed. Rep. of Germany

[21] Appl. No.: 961,709

[22] Filed: Nov. 17, 1978

[30] Foreign Application Priority Data

Nov. 21, 1977 [DE] Fed. Rep. of Germany ....... 2751902

[51] Int. Cl.$^2$ .............................................. A61K 37/48
[52] U.S. Cl. ................................................... 424/94
[58] Field of Search .......................................... 424/94

[56] References Cited

U.S. PATENT DOCUMENTS

| | | | |
|---|---|---|---|
| 2,834,710 | 5/1958 | Baumgarten et al. | 424/94 |
| 2,878,123 | 3/1959 | Beuk et al. | 424/94 |
| 2,906,621 | 9/1959 | Catron | 424/94 |
| 2,988,448 | 6/1961 | Hollenbeck | 424/94 |
| 3,455,696 | 7/1969 | Ukita et al. | 426/43 |
| 3,674,644 | 7/1972 | Yokotsuka et al. | 195/65 |
| 3,677,898 | 7/1972 | Mitsugi et al. | 195/62 |
| 4,062,732 | 12/1977 | Lehmann et al. | 195/62 |

FOREIGN PATENT DOCUMENTS

| | | | |
|---|---|---|---|
| 7302390 | 8/1974 | France | 424/94 |
| 46-23622 | 6/1971 | Japan | 424/94 |
| 1082206 | 9/1967 | United Kingdom | 424/94 |

OTHER PUBLICATIONS

*Chem. Abstr.,* vol. 75 (1971), 108713x; vol. 83, 1975 146220g.

*Primary Examiner*—Frederick E. Waddell
*Attorney, Agent, or Firm*—Hammond & Littell, Weissenberger and Muserlian

[57] ABSTRACT

Animal feeds based on carbohydrates, protein and fats containing from 5 to 100 ppm of one of the antibiotics avoparcin or spiramycin and a content of proteolytic enzymes in such an amount that the enzymatic activity is from 0.05 to 2.5 mTU/gm of said animal feed.

13 Claims, No Drawings

ANIMAL FEEDS CONTAINING A MIXTURE OF AVOPARCIN OR SPIRAMYCIN AND PROTEOLYTIC ENZYMES

BACKGROUND OF THE ART

High-potency animal feeds, as they are normally used today in intensive animal raising, contain a number of additives of prophylactic and/or nutritive effect. These include, among others, antibiotics and enzymes. While the use of antibiotics has found acceptance in mixed feeds of all kinds, enzymes are not as yet used on a large scale in the field.

Thus, U.S. Pat. No. 4,062,732 suggest the use of certain acid proteases in feed, and U.S. Pat. No. 3,455,696 suggest the use of procaine penicillin, dehydrostreptomycin or tetracycline and an acid protease in feeds.

The feed mixtures used in modern intensive animal raising programs are generally optimized in all nutrient components to the extent that further improvement does not seem readily possible.

OBJECTS OF THE INVENTION

An object of the present invention is the development of a mixture of antibiotics and enzymes which will improve the present efficiency of animal feeds.

Another object of the present invention is the development of a high efficiency animal feed based on carbohydrates, protein and fats and containing from 5 to 100 ppm of one of the antibiotics avoparcin or spiramycin and a content of proteolytic enzymes in such an amount that the enzymatic activity is from 0.05 to 2.5 mTU/gm of said animal feed.

A further object of the invention is the development of a method for efficient rearing of animals comprising feeding animals a high efficiency animal feed based on carbohydrates, protein and fats and containing from 5 to 100 ppm of one of the antibiotics avoparcin or spiramycin and a content of proteolytic enzymes in such an amount that the enzymatic activity is from 0.05 to 2.5 mTU/gm of said animal feed.

These and other objects of the invention will become more apparent as the description thereof proceeds.

DESCRIPTION OF THE INVENTION

It has been surprisingly found that even optimally composed high-potency (high efficiency) feeds can be further improved with respect to feed utilization and/or the weight gain attainable therewith by adding to these feeds certain antibiotics together with proteolytic enzymes, particularly acid proteases.

The subject of the invention, accordingly, is an animal feed mixture based on carbohydrates, protein, and fats and optionally the customary additives, characterized by a content of 5 to 100 ppm of one of the antibiotics avoparcin or spiramycin and a quantity of proteolytic enzymes such that an enzymatic activity of 0.05 to 2.5 mTU/gm is present.

More particularly, the present invention relates to a high efficiency animal feed based on carbohydrates, protein and fats and containing from 5 to 100 ppm of an antibiotic selected from the group consisting of avoparcin and spiramycin and a content of proteolytic enzymes, particularly acid proteolytic enzymes, in such an amount that the enzymatic activity is from 0.05 to 2.5 mTU/gm of said animal feed; as well as a method for efficient rearing of animals comprising feeding animals a high efficiency animal feed based on carbohydrates, protein and fats and containing from 5 to 100 ppm of an antibiotic selected from the group consisting of avoparcin and spiramycin and a content of proteolytic enzymes, particularly acid proteolytic enzymes, in such an amount that the enzymatic activity is from 0.05 to 2.5 mTU/gm of said animal feed.

The antibiotic avoparcin belongs to the glycopeptide group. It is produced from a strain of Streptomyces candidus and has a molecular weight of approximately 1500 and an average composition of the empirical formula

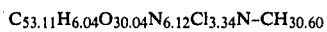

The antibiotic spiramycin belongs to the macrolide group and is produced from a strain of *Streptomyces ambofaciens.*

The antibiotics comprises a combination of 3 bases having the empirical formulae:

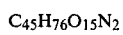

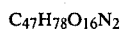

Suitable proteolytic enzymes to be employed according to the invention are obtained above all by culturing microorganisms and separation of the enzymes produced from the culture solutions. The processes for this are known. Proteolytic enzymes can be used as produced, for example, from *Bacillus licheniformis, Bacillus natta, Bacillus subtilis,* etc. Especially preferred are acid proteases, e.g., from *Aspergillus niger* or those described in U.S. Pat. Nos. 3,674,644 and 3,677,898. Acid proteases from the genus Tramates or from *Rhizopus rhizopodiformis* according to U.S. Pat. No. 4,062,732 are particularly preferred. Such proteases have a particularly wide spectrum of action in the weakly acid range between pH 2.5 and 6.5. These acid proteases preferably have a pH range of 50% of maximum activity of between a pH of 2.5 and a pH of 6.5.

Commercial feed mixtures are optimally composed for the special needs of the various animal species. They are customarily based on carbohydrates, proteins and fats with optional customary feed supplements or additives. The carbohydrates are chiefly from cereal components, corn or the like. The protein carriers are primarily extracted soybean meal pellets, fish meals, animal body meal, bran and the like. Essential amino acids which are lacking, for example, methionine, can be added. The fats are employed in the form of plant or animal fats, or added in the form of waste fats. For body building, there are added further salts, such as dicalcium phosphate, calcium carbonate, and common salts. Optionally, the feed mix is balanced by the addition of trace elements, vitamins, ballast substances, etc. Also substances produced fermentatively, such as single cell proteins from petroleum fractions or alcohols, various yeasts, algae protein or others, possibly also substances recovered from waste materials, may be component part of the feed formulation, in part to a considerable degree.

The animal feed mixtures of the invention contain in addition to the usual components adapted for certain animal species or feed use, additionally 5 to 100 ppm, preferably 5 to 20 ppm, of one of the antibiotics avoparcin or spiramycin and the proteolytic enzymes in a quantity such that the enzymatic activity is from 0.05 to 2.5 mTU/gm, preferably 0.2 to 0.5 mTU/gm. In particular, a combination of one of the above-mentioned antibiotics and an acid fungus protease or respectively protease mixture is employed. The weight gain or, respectively the improvement in the feed utilization achieved thereby, is up to several percent in comparison with corresponding control mixtures containing only one of the antibiotics.

The active combination of avoparcin or spiramycin and proteolytic enzymes is successful especially in feed for fattening chickens (broiler production). However, it can be useful also for all other kinds of animals where the use of antibiotics alone is already of advantage, for example, in hog fattening and the rearing of piglets.

At the higher usage levels the active combination of the mentioned antibiotics and enzymes is successful especially in piglet starter and hog fattening feeds.

The antibiotic is expediently added to the feed in the form of a premix, for example, combined with extracted soybean meal pellets. When using mixed meal type feed compositions, the enzyme component is also applied as a premix. Here, as carrier substance, any feed component can be used, for example, again extracted soybean meal pellets. When employing steam-tempered pelletizing of animal feeds, the admixture of the enzymes must occur in suitable stabillized form, to prevent deactivation by moisture and heat during the pelletizing. Such a method is the subject, for example, of U.S. patent application Ser. No. 760,358, filed Jan. 19, 1977.

To determine the enzymatic activity of the enzyme unit (TU), the proteolytic activity of the protease is ascertained by the known principle of Anson. A suitable diluted quantity of enzyme solution is incubated for twenty minutes at 40° C. with an equal volume of a 1.2% casein solution, the latter containing 0.6% lactic acid, 6 mols of urea and 0.1 mol of citric or acetic acid. The pH value of the casein solution is adjusted to 4.5 by addition of 2 N sodium hydroxide solution. After the incubation, the procedure is to admix with 0.4 N trichloroacetic acid in the volumetric ratio 1:1. The forming precipitate of undigested casein is filtered and the protein cleavage products formed during degradation are ascertained in the filtrate by any method of protein determination. Suitable for this is, for example, the method described by Layne in Method of Enzymology 3 (1957), pages 448 ff.

For each test sample a blank value must be produced, wherein first trichloroacetic acid and then casein solution is added. This blank value indicates, in addition to the reagent blank value, the proportion of peptides of low molecular weight already present before the digestion in the enzyme solution. The difference between main and blank value is then compared, following the indicated method, with the extinction, which is given by a predetermined amount of tyrosine. This amount of tyrosine is then a measure of the proteolytic activity of the enzyme being determined. The enzyme unit (TU) is that amount of enzyme which releases in one minute from the casein solution the cleavage products which have the same extinction value as a 1 M tyrosine solution. It is customary to express this in $mTU = 10^{-3}$ TU.

The following examples are illustrative of the invention without being limitative in any respect.

EXAMPLE 1

3840 day-old free-range fattening chicks (sexed, male:female = 1.1) of Ross origin were fed for 6 weeks with feed mixtures of the same composition, but
(a) without an addition of antibiotic or enzyme
(b) with an addition of 10 ppm of avoparcin (AVP)
(c) with an addition of 10 ppm of avoparcin and 0.3 mTU/gm of feed of acid proteases (E) from *Aspergillus niger* and *Rhizopus rhizopodiformis*
(d) with an addition of 15 ppm of spiramycin (SPI)
(e) with an addition of 15 ppm of spiramycin and 0.4 mTU/gm of feed of acid proteases from *Aspergillus niger* and *Rhizopus rhizopodiformis* and after conclusions of the test, the end weight and the feed utilization were determined. The "feed utilization" is the ratio of feed consumption to the weight gain.

TABLE I

| Feed composition (%): | |
|---|---|
| Extracted soybean meal pellets | 27.00 |
| Corn | 37.52 |
| Barley | 6.00 |
| Zein | 3.00 |
| Fish meal | 3.80 |
| Soya oil | 6.98 |
| Wheat | 4.20 |
| Wheat flour | 3.00 |
| Alfalfa meal | 5.00 |
| L-lysine | 0.03 |
| DL methionine | 0.07 |
| Dicalcium phosphate | 0.20 |
| Calcium carbonate | 0.50 |
| Premixture of trace elements, vitamins and coccidiostatic | 2.50 |
| Test premixture | 0.20 |
| | 100.00 |

TABLE II

| | RESULTS | | | | |
|---|---|---|---|---|---|
| | (a) Without additive | (b) With AVP | (c) AVP + E | (d) With SPI | (e) With SPI + E |
| End Weight (gm) | 1508 | 1597 | 1586 | 1549 | 1560 |
| Feed Utilization | 1.91 | 1.84 | 1.81 | 1.88 | 1.86 |

AVP: avoparcin
SPI: spiramycin
E: Proteolytic enzymes from the said microorganisms.

EXAMPLE 2

4456 day-old free-range fattening chicks (sexed, male:female = 1:1) of Hubbard origin were fed for 46 days with feed mixtures of the same composition, but
(a) with an addition of 15 ppm of avoparcin (AVP)
(b) with an addition of 15 ppm of avoparcin and 0.45 mTU/gm of feed of acid proteases from *Aspergillus niger* (E)
(c) with an addition of 10 ppm of spiramycin (SPI)
(d) with an addition of 10 ppm of spiramycin and 0.33 mTU/gm of feed of acid proteases from *Aspergillus niger* and *Rhizopus rhizopodiformis* and, after the test has been concluded, the end weight and feed utilization was determined. The term "feed utilization" refers to the ratio of feed consumption:-growth.

TABLE III

| Feed composition %: | |
| --- | --- |
| Corn | 57.02 |
| Dicalcium phosphate | 0.71 |
| Fish meal | 2.07 |
| Fat | 5.00 |
| Feed grade calcium carbonate | 0.55 |
| Molasses | 1.00 |
| DL methionine | 0.15 |
| Soybean meal pellets | 28.25 |
| Animal body meal | 4.00 |
| Cattle salt, iodized | 0.25 |
| Premixture of vitamins, trace elements and coccidiostatic | 1.00 |
| | 100.00 |

TABLE IV

| | RESULTS | | | |
| --- | --- | --- | --- | --- |
| | (a) With AVP | (b) With AVP + E | (c) With SPI | (d) With SPI + E |
| End Weight (gm) | 1770 | 1766 | 1718 | 1732 |
| Feed Utilization | 1.85 | 1.79 | 1.88 | 1.81 |

AVP: avoparcin
SPI: spiramycin
E: Proteolytic enzymes from the said microorganisms.

EXAMPLE 3

3 Lots, each of 10 piglets weighing from approximately 7 to 20 kg were fed with a pelletized rearing feed of identical composition but which contained (a) an addition of 50 ppm avoparcin (AVP)
(b) an addition of 50 ppm avoparcin and 0.4 mTU/g of acid proteases from *Rhizophus rhizopodiformis* and *Aspergillus niger* (E)

The animals were kept in flat cages, 10, 6 males and 4 females in each case, under SPF conditions (specific pathogenic free). They were fed ad libitum.

The initial weight and final weight, and the feed utilization, were determined by test parameters. "Feed utilization" refers to the ratio of feed consumption to weight increase.

TABLE V

| Feed composition (%): | |
| --- | --- |
| Low grade wheat flour | 20.5 |
| Barley | 32.0 |
| Soybean meal pellets | 24.0 |
| Oats | 10.0 |
| Alfalfa meal | 5.0 |
| Feed yeast | 2.0 |
| Soya oil | 1.8 |
| Feed grade calcium phosphate | 1.5 |
| Feed grade calcium carbonate | 0.8 |
| Premixture of vitamines and trace elements | 2.4 |
| | 100.00 |

TABLE VI

| | (a) With AVP | (b) With AVP + E |
| --- | --- | --- |
| Daily growth | 287 | 344 |
| Feed utilization | 2.11 | 2.00 |

AVP: avoparcin
E: Proteolytic enzymes from the said microorganisms.

The preceding specific embodiments are illustrative of the practice of the invention. It is to be understood, however, that other expedients known to those skilled in the art or disclosed herein may be employed without departing from the spirit of the invention or the scope of the appended claims.

I claim:

1. A high efficiency animal feed based on carbohydrates, protein and fats and containing from 5 to 100 ppm of an antibiotic selected from the group consisting of avoparcin and spiramycin and a content of proteolytic enzyme selected from the acid proteases of *Aspergillus niger* and *Rhizopus rhizopodiformis*, or a mixture thereof, in such an amount that the enzymatic activity is from 0.05 to 2.5 mTU/gm of said animal feed.

2. The animal feed of claim 1 wherein said acid proteolytic enzyme is an acid protease with a wide spectrum of action in the range of between a pH of 2.5 and 6.5.

3. The animal feed of claim 2 wherein said acid protease has a pH range of 50% of maximum activity of between a pH of 2.5 and a pH of 6.5.

4. The animal feed of claim 1 wherein said enzymatic activity is from 0.2 to 0.5 mTU/gm of said animal feed.

5. The animal feed of claim 1 wherein said antibiotic is avoparcin and is present in an amount of from 5 to 20 ppm.

6. The animal feed of claim 1 wherein said antibiotic is spiramycin and is present in an amount of from 5 to 20 ppm.

7. A method for efficient rearing of animals comprising feeding animals a high efficiency animal feed based on carbohydrates, protein and fats and containing from 5 to 100 ppm of an antibiotic selected from the group consisting of avoparcin and spiramycin and a content of proteolytic enzyme selected from the acid proteases of *Aspergillus niger* or *Rhizopus rhizopodiformis*, or a mixture thereof, in such an amount that the enzymatic activity is from 0.05 to 2.5 mTU/gm of said animal feed.

8. The method of claim 7 wherein said proteolytic enzyme is an acid protease with a wide spectrum of action in the range of between a pH of 2.5 and 6.5.

9. The method of claim 8 wherein said acid protease has a pH range of 50% of maximum activity of between a pH of 2.5 and a pH of 6.5.

10. The method of claim 7 wherein said enzymatic activity is from 0.2 to 0.5 mTU/gm of said animal feed.

11. The method of claim 7 wherein said antibiotic is avoparcin and is present in an amount of from 5 to 20 ppm.

12. The method of claim 7 wherein said antibiotic is spiramycin and is present in an amount of from 5 to 20 ppm.

13. A method for improving the growth producing characteristics of an animal feed which comprises adding thereto from 5 to 100 ppm of an antibiotic selected from the group consisting of avoparcin and spiramycin and an amount of proteolytic enzyme selected from the acid proteases of *Aspergillus niger* or *Rhizopus rhizopodiformis*, or a mixture thereof, such that enzymatic activity is from 0.05 to 2.5 mTU/gm of said animal feed.

* * * * *